(12) United States Patent
Davies et al.

(10) Patent No.: US 6,384,244 B2
(45) Date of Patent: May 7, 2002

(54) PROCESS FOR PREPARING CIS-AMINOCHROMANOLS

(75) Inventors: Ian Davies, Princeton; Karl Hansen, Atlantic Highlands; Paul N. Devine, Lincroft; Louis Matty, Jr., Hillsborough; Yuan Cheng, Edison, all of NJ (US); Philippe M. Rabbat, Baie d'Urfe (CA)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/853,796

(22) Filed: May 11, 2001

Related U.S. Application Data

(60) Provisional application No. 60/205,011, filed on May 18, 2000, provisional application No. 60/215,693, filed on Jun. 30, 2000, and provisional application No. 60/216,051, filed on Jul. 5, 2000.

(51) Int. Cl.$^7$ ............................................. C07D 311/04
(52) U.S. Cl. ....................................................... 549/399
(58) Field of Search .......................................... 549/399

(56) References Cited

U.S. PATENT DOCUMENTS

| | | | |
|---|---|---|---|
| 5,413,999 | A | 5/1995 | Vacca et al. |
| 5,905,156 | A | 5/1999 | Manley |
| 6,057,479 | A | 5/2000 | Mitamura et al. |

FOREIGN PATENT DOCUMENTS

| | | |
|---|---|---|
| EP | 0 434 365 | 6/1991 |

OTHER PUBLICATIONS

R. Bognar et al., "Stereochemistry of Flavan–3,4–Diols", Tetrahedron, vol. 19., pp. 391–394 (1963).

R. Bognar et al., "A New Method for the Preparation of 4–hydroxyflavins", Tetrahedron Letters, No. 19, pp. 4–8, (1959).

D. Julian et al., "Synthesis of [1] Benzopyrano [3,4–b] [1,4] oxazines as Potential Antidepressants", J. Heterocyclic Chem., vol. 12, pp. 1179–1182 (1975).

A. Ghosh et al., "Stereoselective Reduction of Alpha–Hydroxy Oxime Ethers: A Convenient Route to Cis–1, 2–Amino Alcohols", Tetrahedron Letters, vol. 32, pp. 711–714 (1991).

H. Kajiro et al., "A Practical Synthesis of (IS, 2R)–1–Amino–2–indanol, a Key Component of HIV Protease Inhibitor, Indinavir", Synlett, pp. 51–52 (1998).

C. Huebner et al., "The Azodiformate Adduct of Indene and the Stereochemistry of Some 1,2–Disubstituted Indans", J. Organic Chemistry, vol. 35, pp. 1149–1154 (1970).

*Primary Examiner*—Amelia Owens
(74) *Attorney, Agent, or Firm*—Kenneth R. Walton; Valerie J. Camara

(57) ABSTRACT cis-aminochromanols are obtained in high yield and with high selectivity over their trans counterparts by hydrogenating the corresponding oximes in the presence of a catalyst and an acid selected from HBr, HCl, and organic sulfonic acid. The cis-aminochromanols can be employed as intermediates in the production of HIV protease inhibitors which are useful for treating HIV infection and AIDS.

30 Claims, No Drawings

PROCESS FOR PREPARING CIS-AMINOCHROMANOLS

This application claims the benefit of U.S. Provisional Application No. 60/205,011, filed May 18, 2000, U.S. Provisional Application No. 60/215,693, filed Jun. 30, 2000 and U.S. Provisional Application No. 60/216,051, filed Jul. 5, 2000, the disclosures of which are herein incorporated by reference in their entireties.

FIELD OF THE INVENTION

The present invention relates to the preparation of cis-aminochromanols by reduction of the corresponding α-hydroxyoximes. cis-Aminochromanols are useful as intermediates in the preparation of HIV protease inhibitors.

References are made throughout this application to various published documents in order to more fully describe the state of the art to which this invention pertains. The disclosures of these references are hereby incorporated by reference in their entireties.

BACKGROUND OF THE INVENTION cis-Aminochromanols are useful as intermediates in the preparation of HIV protease inhibitor compounds, which can be used to treat HIV infection, AIDS and ARC. EP 434,365 discloses, inter alia, a series of N-substituted 2(R)-((morpholinyl-ethoxy)phenylmethyl)-5(S)-((dimethylethoxycarbonyl)amino)-4(S)-hydroxy-6-phenylhexanamide derivatives which are useful as HIV protease inhibitors, including inhibitors prepared using cis-aminochromanol. In particular, reference is made to Example 21 of EP '365. U.S. Pat. No. 5,413,999 discloses certain N-substituted 2(R)-phenylmethyl-4(S)-hydroxypentaneamide derivatives which are useful as HIV protease inhibitors, including inhibitors which can be prepared from cis-aminochromanol. Reference is made, for example, to Table 1 of US '999, the third entry in cols. 33–34.

Bognar et al., *Tetrahedron* 1963, 19: 391–394, discloses the preparation of 4-amino-3-hydroxyflavan by the hydrogenation of the corresponding oxime in the presence of $PtO_2$ at atmospheric pressure in warm aqueous (80%) acetic acid. Bognar et al., *Tet. Letters* 1959, No. 19: 4–8, has a similar disclosure.

Julian et al., *J. Het. Chem.* 1975, 12: 1179–1182, discloses the preparation of cis-4-aminochroman-3-ol by reaction of 2-oxo-1,3a,4,9b-tetrahydro-2H[1]benzo-pyrano[4,3-d]oxazole with methanolic potassium hydroxide. EP 434,365 discloses substantially the same preparation in Example 21, Steps A and B.

Ghosh et al., *Tet. Letters* 1991, 32: 711–714, discloses the preparation of 4-aminothiochroman-3-ol by the reduction of the corresponding α-hydroxy benzyloxime with borane in tetrahydrofuran. It is further disclosed that borane reduction of an equilibrium mixture (3:2) of the anti and syn oximes afforded a 90/10 mixture of the cis/trans 4-aminothiochroman-3-ols.

U.S. Pat. No. 6,057,479 (Mitamura et al.) discloses the preparation of cis-1-amino-2-indanol by the catalytic hydrogenation of 2-hydroxy-1-indanone oxime in methanol. Example 21 of US '479 discloses the hydrogenation in the presence of Pd black and HCl to give an aminoindanol product having a cis/trans selectivity of 95.5:4.5. Examples 22–23 report similar results for analogous hydrogenations using Pd/C and Pd/alumina. Example 24 discloses an analogous hydrogenation using Pd black and aqueous HBr to provide 1-amino-2-indanol product with a cis/trans ratio of 95.6:4.4. Results substantially the same as in Example 24 are also reported in Kajiro et al., *SYNLETT* 1998, p. 51.

SUMMARY OF THE INVENTION

The present invention is directed to a process for preparing cis-4-aminochroman-3-ols via oxime hydrogenation. The process of the present invention has unexpectedly been found to afford cis-aminochromanol in high yields and with a relatively high selectivity relative to the trans isomer. More particularly, the present invention is a process for preparing a cis-aminochromanol of Formula (I):

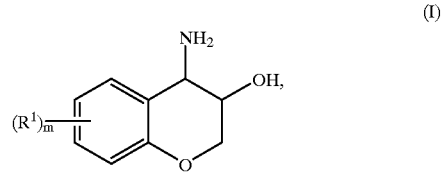

(I)

which comprises:
(A) hydrogenating in the presence of a catalyst a mixture comprising an oxime of Formula (II):

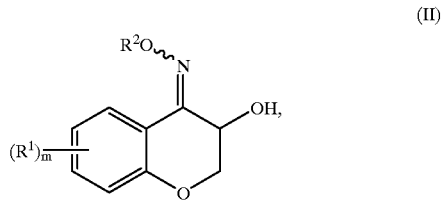

(II)

solvent, and an acid selected from the group consisting of (i) HBr, (ii) HCl, and (iii) organic sulfonic acids; wherein each $R^1$ is independently halo, $C_1$–$C_6$ alkyl, halogenated $C_1$–$C_6$ alkyl, $C_1$–$C_6$ alkoxy, halogenated $C_1$–$C_6$ alkoxy, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^a$CO—$NR^aR^b$, —$S(O)_p$—$R^a$, wherein p is an integer from 0 to 2, —$S(O)_2$—$NR^aR^b$, —$NR^aS(O)_2$—$R^b$, or —$NR^aS(O)_2$—$NR^aR^b$;

$R^2$ is
(1) hydrogen;
(2) $C_1$–$C_6$ alkyl;
(3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl, or phenyl;
(4) $C_3$–$C_8$ cycloalkyl;
(5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl;
(6) phenyl; or
(7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo;

each $R^a$ and $R^b$ is independently hydrogen, $C_1$–$C_4$ alkyl, or $(CH_2)_{0-3}CF_3$; and m is an integer from 0 to 4.

In one embodiment, the present invention further comprises:

(B) treating the hydrogenated mixture with base to provide free amine.

The process of the present invention has distinct advantages over known methods for producing aminochromanols. For example, the $PtO_2$-catalyzed hydrogenation disclosed in Bognar et al. (cited above) employs acetic acid, which has poor selectivity for the cis product over the trans. The preparation of aminothiochromanol disclosed in Ghosh et al. (cited above) requires reduction of a benzyloxime reactant with borane, which is a relatively expensive reducing agent, and has a relatively poor yield and poor cis/trans selectivity. On the other hand, the hydrogenation process of the present invention can achieve relatively high yields and high cis over trans selectivity using inexpensive reagents (i.e., $H_2$ and HBr, HCl, or an organic sulfonic acid) and a reusable catalyst (e.g., palladium).

The process of the invention is distinct from the hydrogenation chemistry disclosed in U.S. Pat. No. 6,057,479, which is limited to the preparation of cis-1-amino-2-indanol. Furthermore, the C6:C5O chromanyl ring system is much more flexible than the relatively rigid C6:C5 indanyl system, and thus has access to a number of low energy conformations that would not be available to the indanyl. Accordingly, the relative high cis/trans selectivity for the aminoindanol product disclosed in US '479 is not predictive of the selectivity that can be achieved for an aminochromanol product prepared using the analogous chemistry. Further evidence of the distinctiveness of the process of the invention with respect to US '479 is that US '479 discloses essentially the same cis/trans selectivity for both HCl and HBr, whereas the process of the invention can achieve much higher cis-trans selectivity for HBr, than for HCl (see Examples 3 and 5 below).

Other embodiments, aspects and features of the present invention are either further described in or will be apparent from the ensuing description, examples and appended claims.

DETAILED DESCRIPTION OF THE INVENTION

The present invention includes a process for preparing cis-amino-chromanols by catalytically hydrogenating the corresponding α-hydroxyoxime in the presence of an acid. This process is set forth in the Summary of the Invention as Step A.

In this process, each group $R^1$ in the definition of Compounds I and II is independently halo, $C_1$–$C_6$ alkyl, halogenated $C_1$–$C_6$ alkyl, $C_1$–$C_6$ alkoxy, halogenated $C_1$–$C_6$ alkoxy, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_p$—$R^a$, wherein p is an integer from 0 to 2, —$S(O)_2$—$NR^aR^b$, —$NR^aS(O)_2$—$R^b$, or —$NR^aS(O)_2$—$NR^aR^b$. In one embodiment, each $R^1$ is independently halo, $C_1$–$C_6$ alkyl, halogenated $C_1$–$C_6$ alkyl, $C_1$–$C_6$ alkoxy, or halogenated $C_1$–$C_6$ alkoxy. In another embodiment, each $R^1$ is independently halo, $C_1$–$C_4$ alkyl, halogenated $C_1$–$C_4$ alkyl, $C_1$–$C_4$ alkoxy, or halogenated $C_1$–$C_4$ alkoxy. In still another embodiment, each $R^1$ is independently chloro, fluoro, $C_1$–$C_4$ alkyl, fluorinated $C_1$–$C_4$ alkyl, $C_1$–$C_4$ alkoxy, or fluorinated $C_1$–$C_4$ alkoxy. In still another embodiment, each $R^1$ is fluoro, $C_1$–$C_4$ alkyl, $(CH_2)_{0-3}CF_3$, $C_1$–$C_4$ alkoxy, or $O(CH_2)_{0-3}CF_3$. In yet another embodiment, each $R^1$ is independently fluoro, methyl, ethyl, trifluoromethyl, 2,2,2-trifluoroethyl, methoxy, ethoxy, trifluoromethoxy, or 2,2,2-trifluoroethoxy.

In the definition of $R^1$, each $R^a$ and $R^b$ is independently hydrogen, $C_1$–$C_4$ alkyl, or $(CH_2)_{0-3}CF_3$. In one embodiment, each $R^a$ and $R^b$ is independently hydrogen, methyl, ethyl, or $CF_3$.

The integer m defines the number of $R^1$ groups which may be present in Compounds I and II and has a value in the range of from 0 to 4. In other embodiments, m is 0 to 3; or is 1 to 3; or is 0 to 2; or is 1 to 2; or is 0 to 1; or is 0. An aspect of the process of the invention is the process as set forth above wherein m is zero.

In the process of the invention, the group $R^2$ in the definition of Compound II is (1) hydrogen; (2) $C_1$–$C_6$ alkyl; (3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl or phenyl; (4) $C_3$–$C_8$ cycloalkyl; (5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl; (6) phenyl; or (7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo. In one embodiment, $R^2$ is (1) hydrogen; (2) $C_1$–$C_4$ alkyl; or (3) $C_1$–$C_4$ alkyl substituted with one or more substituents, each of which is independently halo, cyano, $C_1$–$C_4$ alkoxy, $C_1$–$C_4$ haloalkoxy, $C_3$–$C_8$ cycloalkyl or phenyl. In other embodiments, $R^2$ is hydrogen, methyl, ethyl, phenyl, or benzyl; or is hydrogen.

The α-hydroxyoxime of Formula II can be prepared in accordance with methods known in the art, such as by reacting the corresponding α-hydroxyketone with hydroxylamine hydrochloride or with a suitable derivative thereof (e.g., O-alkyloxy-, O-cycloalkyloxy-, and O-phenyloxyamine hydrochlorides). The α-hydroxyketone can be obtained by hydrolysis of the corresponding α-hydroxy dimethylketal, which in turn can be prepared from the chroman-4-one via the Moriarty reaction, which is described in Moriarty et al., *Tet. Letters* 1981, 22: 1283–1286 and Moriarty et al., *Synth. Commun.* 1984, 14: 1373–1378. The α-hydroxyketone can also be prepared in accordance with methods described in Davis et al., *J. Org. Chem.* 1990, 55: 3715–3717; Rubottom et al., *J. Org. Chem.* 1978, 43: 1599–1602; and Hassner et al., *J. Org. Chem.* 1975, 40: 3427–3429.

The acid employed in Step A can be HBr, HCl, or an organic sulfonic acid. Exemplary sulfonic acids are methanesulfonic acid, trifluoromethylsulfonic acid, ethanesulfonic acid, benzenesulfonic acid, p-toluenesulfonic acid, p-acetamidobenzenesulfonic acid, and dodecylbenzenesulfonic acid.

In one embodiment, the acid is selected from the group consisting of HBr, HCl, and sulfonic acids of formula $R^*$—$SO_2H$, wherein $R^*$ is $C_1$–$C_6$ alkyl, fluorinated $C_1$–$C_6$ alkyl, phenyl, or substituted phenyl wherein each of the substituents on substituted phenyl is independently $C_1$–$C_{12}$ alkyl, $C_1$–$C_{12}$ haloalkyl, halo, cyano, nitro, $C_1$–$C_6$ alkoxy, $C_2$–$C_8$ alkoxyalkyl, $N(R^cR^d)_2$, and $NR^cCOR^d$; wherein each $R^c$ and $R^d$ is independently hydrogen, $C_1$–$C_6$ alkyl, or $(CH_2)_{0-4}CF_3$. In an aspect of the preceding embodiment, the sulfonic acid is of formula $R^*$—$S_2H$, wherein $R^*$ is $C_{1-C4}$ alkyl or fluorinated $C_1$–$C_4$ alkyl. In another aspect of the preceding embodiment, sulfonic acid is of formula $R^*$—$SO_2H$, wherein $R^*$ is $C_1$–$C_4$ alkyl.

In another embodiment, the acid is HBr, HCl, or methanesulfonic acid. In further embodiments, the acid is HBr or methanesulfonic acid; or is methanesulfonic acid; or is HBr. In a preferred embodiment of the process of the invention, the acid is HBr. In one aspect, HBr is employed as aqueous HBr, such as 48% HBr.

Suitable solvents for Step A can be selected from the group consisting of $C_3$–$C_{12}$ linear and branched alkanes, $C_1$–$C_6$ linear and branched halogenated alkanes, $C_5$–$C_7$ cycloalkanes, $C_6$–$C_{10}$ aromatic hydrocarbons, dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, and $C_1$–$C_6$ alkyl alcohols. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, methanol, ethanol, n- and iso-propanol, and tert-butyl alcohol.

In one embodiment, the solvent is selected from the group consisting of $C_2$–$C_6$ linear and branched halogenated alkanes, dialkyl ethers wherein each alkyl is independently a $C_1$–$C_4$ alkyl, $C_4$–$C_6$ cyclic ethers and diethers, and $C_1$–$C_4$ alkyl alcohols. In an aspect of the preceding embodiment, the solvent is a $C_1$–$C_4$ alkyl alcohol. In another aspect of the preceding embodiment, the solvent is methanol.

The solvent can also be a mixture comprising water and an organic co-solvent. Suitable co-solvents include the organic solvents set forth in the preceding two paragraphs. In one embodiment, the co-solvent is a $C_1$–$C_6$ monohydric alcohol. In an aspect of this embodiment, the co-solvent is methanol or ethanol. The water can comprise from about 5 to about 95 volume percent based on the total volume of solvent. It has been found, however, that significant amounts of water (i.e., more than about 20 volume percent) can reduce the cis/trans selectivity of the hydrogenation. The use of 1:2 methanol/water solvent systems with HBr, for example, has been found to reduce selectivity dramatically compared to the use of methanol alone (e.g., 11:1 v. 23:1). Accordingly, in a preferred embodiment, the amount of water in the water-organic co-solvent mixture (e.g., water/methanol) is no more than about 20 vol %.

The hydrogenation of the oxime II can be conducted over a wide range of temperatures, although the temperature is typically in the range of from about –25 to about 200° C. (e.g., from about –20 to about 100°). In one embodiment, the temperature is in the range of from about –10 to about 20° C. In another embodiment, the temperature is from about –5 to about 5° C.

The pressure is not a critical aspect of the process of the invention, although atmospheric and superatmospheric pressures tend to be expedient. In one embodiment, the pressure is at least about 2 psig (115 kPa). In another embodiment, the pressure is in the range of from about 10 psia (68.9 kPa) to about 10,000 psia (68,950 kPa) (e.g., from about 50 psia (345 kPa) to about 1,000 psia (6,895 kPa)).

In one embodiment, the hydrogenation is conducted at a temperature in the range of from about –20 to about 100° C. and at a pressure of from about 2 psig (115 kPa) to about 1000 psig (6996 kPa). In another embodiment, the hydrogenation is conducted at a temperature in the range of from about –5 to about 20° C. and at a pressure in the range of from about 10 psig (167 kPa) to about 500 psig (3549 kPa). In still another embodiment, the hydrogenation is conducted at a temperature in the range of from about –10 to about 10° C. and at a pressure in the range of from about 10 psig (170 kPa) to about 100 psig (791 kPa).

Any catalyst which is capable of expediting the hydrogenation of the oxime functional group in Compound II may be employed in the process of the invention. Typically, the catalyst comprises one or more of the Group VIII metals as set forth in the Periodic Table of the Elements (see, e.g., the 78th edition of the *Handbook of Chemistry and Physics,* CRC Press (1997)). Suitable hydrogenation catalysts include palladium, rhenium, rhodium, platinum, or nickel. The catalyst can be supported or unsupported. Suitable catalyst supports include carbon, silica, alumina, silicon carbide, aluminum fluoride, and calcium fluoride. Palladium is particularly suitable for use in the process of the invention. Exemplary palladium catalysts include Pd black (i.e., fine metallic palladium particles) and Pd/C (i.e., palladium on a carbon support). Pd black is an effective catalyst, but results have been found to depend upon on the choice of vendor. Pd/C is a preferred catalyst.

The hydrogen source is typically hydrogen gas, optionally in admixture with a carrier gas that is inert to the process of the invention (e.g., nitrogen or a noble gas such as helium or argon).

The hydrogenation can be carried out in batches or continuously in various types of reactors such as a fixed bed reactor or an agitated slurry reactor in which the slurry of gas, solvent, oxime II, acid, and catalyst is continuously agitated by mechanical or gas means. A suitable reaction vessel for relatively small scale, batch-wise hydrogenations is an autoclave equipped with a stirrer or rocker to agitate the reaction mixture. In a batch process, the order of addition of oxime II, solvent, acid, and hydrogenation catalyst to the reaction vessel (also referred to herein as the reaction "pot") is not critical. The reactants and reagents can, for example, be added concurrently, either together or separately, or they can be added sequentially in any order. In one embodiment, Compound II pre-mixed with the solvent is charged to the reaction vessel followed by addition of the acid, and then the catalyst. The hydrogenation can then be conducted by charging hydrogen gas, optionally in admixture with one or more inert gases, to the vessel containing the mixture comprising oxime II, solvent, acid and catalyst, and then agitating the mixture under reaction conditions.

Any amount of acid, catalyst and hydrogen can be employed which results in the formation of at least some of Compound II. Of course, the maximum conversion of Compound II and maximum yield of Compound I is normally desired, and relative proportions of reactants and reagents suitable for this purpose are typically employed.

The acid is suitably employed in Step A in an amount of at least about 0.5 equivalents per equivalent of Compound II, and is typically employed in an amount of at least about 1 equivalent per equivalent of Compound II. In one embodiment, the acid is employed in an amount in the range of from about 0.5 to about 2 equivalents per equivalent of Compound II. In another embodiment, the amount of acid is in the range of from about 0.75 to about 1.25 equivalents per equivalent of II. In still another embodiment, the amount of acid is in the range of from about 0.95 to about 1.05 equivalents per equivalent of II.

In one aspect of the process, the acid is HBr, the amount of acid is in the range of from about 0.95 to about 1.05 equivalents per equivalent of II, and the hydrogenation temperature is in the range of from about –5 to about 5° C. In another aspect of the process, the catalyst is Pd/C, the acid is HBr, the amount of acid is in the range of from about 0.95 to about 1.05 equivalents per equivalent of II, and the hydrogenation temperature is in the range of from about –5 to about 5° C.

When the level of HBr employed in the process is greater about 1.25 equivalents, hydrogenation should be begun promptly after the addition of the acid to avoid formation of solvoiysis by-products such as, when using methanol solvent,

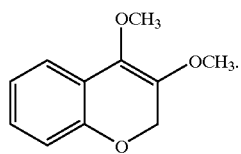

The uptake of hydrogen is not a critical process parameter, although at least a stoichiometric amount of hydrogen gas is typically employed.

Any amount of catalyst can be employed which results in the formation of at least some of Compound I. The amount of catalyst employed in step A is suitably at least about 0.01 mole percent transition metal (e.g., Pd), and is typically in the range of from about 0.01 to about 5 (e.g., from about 0.1 to about 5) mole percent transition metal, based on the total moles of transition metal and Compound I. In one embodiment, the amount of catalyst is in the range of from about 1 to about 5 (e.g., from about 2 to about 3) mole percent transition metal. In another embodiment, the catalyst comprises palladium (e.g., Pd/C), and the amount of palladium catalyst is in the range of from about 1 to about 5 mole percent. In an aspect of the preceding embodiment, the Pd catalyst is present in an amount in the range of from about 2 to about 3 mole percent.

If desired, the progress of the reaction in Step A can be followed by monitoring the disappearance of a reactant (i.e., Compound II or $H_2$) and/or the appearance of the product using such analytical techniques as TLC, HPLC, NMR or GC.

The present invention also includes a process which comprises the oxime hydrogenation as heretofore described (Step A), followed by treatment of the hydrogenated product mixture with base to provide a free amine (Step B).

Any organic or inorganic base can be used in step B which is capable of neutralizing the acidic hydrogenated mixture resulting from step A. Suitable bases include bases selected from the group consisting of alkali metal hydroxides, alkali metal carbonates, alkali metal oxides, $C_1$–$C_6$ alkoxides of alkali metals, alkaline earth metal hydroxides, alkaline earth metal oxides, tetra ($C_1$–$C_4$ alkyl)ammonium hydroxides, and tri-($C_1$–$C_4$ alkyl)amines. Exemplary bases include hydroxides, carbonates, and oxides of lithium, sodium and potassium; methoxides, ethoxides, and n- and isopropoxides of lithium, sodium, and potassium; tetramethyl- and tetraethyl-ammonium hydroxide; triethylamine; and diisopropylethylamine. In one embodiment, the base is selected from the group consisting of alkali metal hydroxides. In an aspect of the preceding embodiment, the base is NaOH or KOH.

The base can be employed in step B in any proportion with respect to Compound I which will at least partially neutralize the acidic hydrogenated mixture from step A, so as provide at least some of Compound II as free base. Typically, however, base is employed in an amount sufficient to achieve complete neutralization. The amount of base employed in step B can suitably be at least about 1 equivalent per equivalent of Compound II, and is typically in the range of from about 1 to about 5 equivalents per equivalent of Compound II. In one embodiment, the amount of base is from about 1 to about 2 equivalents per equivalent of Compound II. In another embodiment, the amount of base is in the range of from about 1 to about 1.5 equivalents per equivalent of Compound II. The base can be charged to the reaction vessel containing the step A hydrogenated mixture, or the hydrogenated mixture can be charged to a vessel containing the base.

Step B is suitably conducted at a temperature in the range of from about –10 to about 110° C., and is typically conducted at a temperature in the range of from about 0 to about 80° C. In one embodiment, the temperature is in the range of from about 10 to about 30° C.

Alternatively, the base treatment of step B can comprise eluting the hydrogenated mixture through a suitable ion exchange column, such as elution through Dowex® (available from Dow Chemical) or Amberlyst-IRA (available from Rohm & Haas).

Following the treatment with base, Compound I can be isolated from the reaction mixture by conventional means, such as by filtration to remove solids, solvent wash, concentration (e.g., by vacuum removal of solvent), and crystallization.

An embodiment of the process of the invention is the process comprising Steps A and B as heretofore described, which further comprises
(C) resolving the S,S- and R,R-isomers of Compound I by
  (c1) forming a solution comprising Compound I, a chiral acid, and solvent, and
  (c2) crystallizing from the solution a salt which contains predominantly either the S,S- or R,R-isomer.

Suitable chiral acids include optically active forms of tartaric acid, mandelic acid, camphoric acid, 10-camphorsulfonic acid, pyroglutamic acid, O,O-diacetyltartaric acid, O,O-dibenzoyltartaric acid, O,O-di-4-toluyltartaric acid, and N-acetyl derivatives of amino acids such as N-acetylleucine.

The solvent can be any organic or inorganic substance, or combinations thereof, which can dissolve Compound I and the chiral acid and is chemically inert thereto. Suitable solvents include water, $C_1$–$C_6$ monohydric alcohols (e.g., methanol, ethanol, n-propanol, n-butanol, n-pentanol, isopropanol, and sec-butyl alcohol), $C_2$–$C_8$ polyhydric alcohols (e.g., ethylene glycol, propylene glycol, and glycerol), $C_1$–$C_4$ nitriles (e.g., acetonitrile and propionitrile), N,N-di-$C_1$–$C_6$ alkyl tertiary amides of $C_1$–$C_6$ alkylcarboxylic acids (e.g., DMF), aliphatic $C_2$–$C_6$ ethers and di-ethers (e.g., ethyl ether, MTBE and dimethoxyethane), and $C_4$–$C_6$ cyclic ethers and di-ethers (e.g., TBF and dioxane). In one embodiment, the solvent is selected from the group consisting of $C_1$–$C_6$ monohydric alcohols, aliphatic $C_2$–$C_6$ ethers and di-ethers and $C_4$–$C_6$ cyclic ethers and di-ethers. In an aspect of the preceding embodiment, the solvent is an alcohol such as methanol or ethanol.

In another embodiment, the solvent is a mixture comprising water and an organic co-solvent. In an aspect of this embodiment, water comprises at least about 5 volume percent of the solvent (e.g., from about 5 to about 95 volume percent) based on the total volume of solvent. In another aspect of this embodiment, the aqueous solvent comprises from about 30 to about 70 volume percent (e.g., from about 40 to about 60 volume percent) water, with the balance of the solvent being organic co-solvent. Suitable co-solvents include the organic solvents set forth in the preceding paragraph. In one embodiment, the co-solvent is a $C_1$–$C_6$ monohydric alcohol. In an aspect of this embodiment, the co-solvent is methanol or ethanol.

The crystallization of the S,S- or R,R-isomer in (c2) can be accomplished using conventional techniques, such as by cooling the solution or by concentrating the solution via vacuum or evaporative removal of solvent. The resulting crystals can then be separated by filtration and followed optionally by the washing and drying of the filter cake.

In one aspect of step C, the chiral acid is (S)-mandelic acid or (R)-mandelic acid. In a preferred aspect of step C, the chiral acid is (S)-mandelic acid, and the crystallized (S)-mandelate salt resulting from (c2) is a salt of the S,S-isomer.

In another aspect, step C further comprises: (c3) recovering a salt which contains predominantly the other of the S,S- and R,R-isomers from the mother liquor, such as by evaporative or vacuum removal of the solvent.

In still another aspect, step C further comprises: (c4) breaking the crystallized salt of the recovered isomer by treating the salt with base. In a typical procedure, the crystallized salt can be slurried in an organic solvent, the slurry mixed with aqueous base resulting in a biphasic mixture, and the organic layer containing the isomer separated from the aqueous layer. The formation of the slurry and the biphasic mixture are suitably conducted at temperatures in the range of from about 0 to about 100° C., and are typically conducted at a temperature of from about 10 to about 60° C. In one embodiment, the temperature is in the range of from about 15 to about 35° C. The base can be any of the bases set forth above in the description of step B. The base can also be an alkanolamine (e.g., ethanolamine), a hydroxylamine (e.g., hydroxylamine per se, N-methylhydroxylamine, N,N-dimethylhydroxylamine, or N-ethylhydroxylamine), or a diamine (e.g., ethylenediamine, tetramethylenediamine, or hexamethylenediamine). The organic solvent can suitably be selected from $C_1-C_{12}$ linear and branched alkanes, $C_1-C_{12}$ linear and branched halogenated alkanes, $C_5-C_{10}$ cycloalkanes, $C_6-C_{14}$ aromatic hydrocarbons, dialkyl ethers wherein each alkyl is independently a $C_1-C_{10}$ alkyl, $C_4-C_8$ dialkoxyalkanes, $C_4-C_8$ cyclic ethers and diethers, $C_6-C_8$ aromatic ethers, $C_2-C_{10}$ dialkyl ketones wherein each alkyl is independently $C_1-C_8$ alkyl, $C_1-C_6$ alkyl esters of $C_1-C_6$ alkylcarboxylic acids, primary $C_1-C_{10}$ alkyl alcohols, secondary $C_3-C_{10}$ alkyl alcohols, tertiary $C_4-C_{10}$ alkyl alcohols, primary amides of $C_1-C_6$ alkylcarboxylic acids, N-$C_1-C_6$ alkyl secondary amides or N,N-di-$C_1-C_6$ alkyl tertiary amides of $C_1-C_6$ alkylcarboxylic acids, $C_2-C_6$ aliphatic nitriles, and $C_7-C_1$ aromatic nitriles. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, acetone, methyl ethyl ketone (MEK), methyl acetate, ethyl acetate, IPAc, ethanol, n- and iso-propanol, tert-butyl alcohol, dimethylformamide (DMF), acetonitrile, propionitrile, benzonitrile, and p-tolunitrile.

In yet another aspect of step C, the crystallized salt is the (S)-mandelate salt of the S,S-isomer; wherein in the salt breaking step, the base is ethanolamine and the breaking of the salt provides an S,S-aminochromanol of Formula (I'):

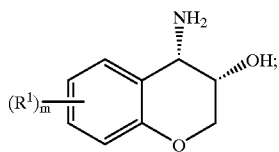

(I')

wherein $R^1$ and m are as heretofore defined.

Another embodiment of the process of the invention is a process for preparing cis-aminochromanol 5:

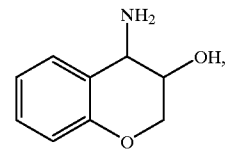

5 which comprises (A) hydrogenating a mixture of oxime 3:

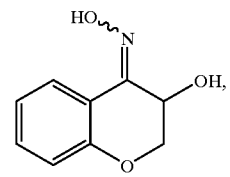

3 and solvent in the presence of a catalyst and in the presence of an acid selected from the group consisting of (i) HBr, (ii) HCl, and (iii) organic sulfonic acids; and (B) treating the hydrogenated mixture with base.

Aspects of the preceding embodiment include the process as set forth, wherein:

(i) the catalyst is a palladium catalyst (e.g., Pd/C);

(ii) the acid is HBr or methanesulfonic acid;

(iii) the acid is HBr (e.g., aqueous HBr);

(iv) the hydrogenation is conducted at a temperature in the range of from about −20 to about 100° C. and at a pressure of at least about 2 psig (115 kPa);

(v) the hydrogenation is conducted at a temperature in the range of from about −5 to about 5° C. and the amount of acid is in the range of from about 0.95 to about 1.05 equivalents per equivalent of 3;

(vi) the process incorporates the combination of (i) and (ii);

(vii) the process incorporates the combination of (i) and (iii);

(viii) the process includes the combination of (i), (ii) or (iii), and (iv); and (ix) the process includes the combination of (i), (ii) or (iii) and (v).

In yet another aspect of the preceding embodiment, the process further comprises:

(C) resolving the S,S-isomer of 5 by
  (c1) forming a solution of 5 with (S)-mandelic acid, and
  (c2) crystallizing from the solution a salt of the S,S-isomer, and optionally
  (c4) breaking the (S)-mandelate salt with ethanolamine to provide S,S-aminochromanol 7:

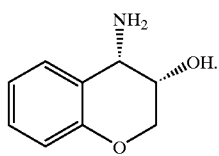

The present invention also includes a process for improving the optical purity of S,S-aminochromanol 7:

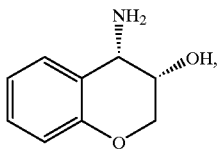

with which at least some R,R-isomer is present, wherein the process comprises:
(a) forming a solution comprising cis-aminochroman-3-ol, (S)-mandelic acid, and solvent;
(b) crystallizing the (S)-mandelate salt from the solution; and
(c) breaking the (S)-mandelate salt with base (e.g., ethanolamine) to provide 7 having greater optical purity.

The bases, solvents, and procedures set forth above for step C are also suitable for the practice of this process.

As used herein, the term "$C_1$–$C_6$ alkyl" (which may alternatively be referred to herein as "$C_{1}$–$C_{6}$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl. Similar terms (e.g., "$C_1$–$C_3$ alkyl") have analogous definitions.

The term "$C_1$–$C_6$ alkoxy" means an —O-alkyl group wherein alkyl is $C_1$ to $C_6$ alkyl as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy. Similar terms (e.g., "$C_1$–$C_3$ alkoxy") have analogous definitions.

The term "halogen" (which may alternatively be referred to as "halo") refers to fluorine, chlorine, bromine and iodine (alternatively, fluoro, chloro, bromo, and iodo).

The term "halogenated $C_1$–$C_6$ alkyl" (which may alternatively be referred to as "$C_1$–$C_6$ haloalkyl") or "$C_{1-6}$ haloalkyl" means a $C_1$ to $C_6$ linear or branched alkyl group as defined above with one or more halogen substituents. The terms "halogenated $C_1$–$C_4$ alkyl" and "halogenated $C_1$–$C_3$ alkyl" have analogous meanings. The term "fluorinated $C_1$–$C_6$ alkyl" (or "$C_1$–$C_6$ fluoroalkyl" or "$C_{1-6}$ fluoroalkyl") means a $C_1$ to $C_6$ linear or branched alkyl group as defined above with one or more fluorine substituents. The terms "fluorinated $C_1$–$C_4$ alkyl" and "fluorinated $C_1$–$C_3$ alkyl" have analogous meanings. Representative examples of suitable fluoroalkyls include the series $(CH_2)_{0-3}CF_3$ and $(CH_2)_{0-2}CF_3$ (i.e., trifluoromethyl, 2,2,2-trifluoroethyl, and 3,3,3-trifluoro-n-propyl), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "halogenated $C_1$–$C_6$ alkoxy" (which may alternatively be referred to as "$C_1$–$C_6$ haloalkoxy" or "$C_{1-6}$ haloalkoxy") means a $C_1$ to $C_6$ linear or branched alkyl group as defined above with one or more halogen substituents. The terms "halogenated $C_1$–$C_4$ alkoxy" and "halogenated $C_1$–$C_3$ alkoxy" have analogous meanings. The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The terms "fluorinated $C_1$–$C_4$ alkoxy" and "fluorinated $C_1$–$C_3$ alkoxy" have analogous meanings. Representative examples include the series $O(CH_2)_{0-3}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Similarly, "$C_2$–$C_6$ alkoxyalkyl" means a linear or branched $C_1$–$C_5$ alkyl group as defined above having as a substituent a $C_1$–$C_5$ alkoxy group as defined above, wherein the alkoxyalkyl group has a total of from 2 to 6 carbon atoms. "$C_2$–$C_4$ alkoxyalkyl" means a linear or branched $C_1$–$C_3$ alkyl group as defined above having as a substituent a $C_1$–$C_3$ alkoxy group as defined above, wherein the alkoxyalkyl group has a total of from 2 to 4 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3$, $(CH_2)_{1-4}OCH_3$, $(CH_2)_{1-3}OCH_3$, $(CH_2)_{1-6}OCH_2CH_3$, and $(CH_2)_{1-4}OCH_2CH_3$.

The term "$C_3$–$C_8$ cycloalkyl" refers to a cyclic ring selected from cyclopropyl, cyclobutyl, cyclopentyl, cyclohexyl, cycloheptyl, and cyclooctyl. "$C_3$–$C_6$ cycloalkyl" has an analogous meaning.

The term "alkali metal" refers to a metal of Group Ia of the Periodic Table, including but not limited to lithium, sodium, and potassium.

The term "alkaline earth metal" refers to a metal of Group IIa of the Periodic Table, including but not limited to magnesium and calcium.

Abbreviations used in the instant specification include the following:
Ac=acetic or acetate
AIDS=acquired immune deficiency syndrome
ARC=AIDS related complex
Bn=benzyl
DCE=1,2-dichloroethane
DME=1,2-dimethoxyethane
DMF=dimethylformamide
DSC=differential scanning calorimetry
IPAc=isopropyl acetate
KF=Karl Fisher titration for water
Me=methyl
MeOH=methanol
MTBE=methyl tert-butyl ether
Ph=phenyl
psia=pounds per square inch (absolute)
psig=pounds per square inch (gauge)
TCE=1,1,2-trichloroethane
TF=tetrahydrofuran
XRPD=X-ray powder diffraction The following examples serve only to illustrate the invention and its practice. The examples are not to be construed as limitations on the scope or spirit of the invention.

EXAMPLE 1

Preparation of cis-Aminochromanol

Step A: Oxime Formation

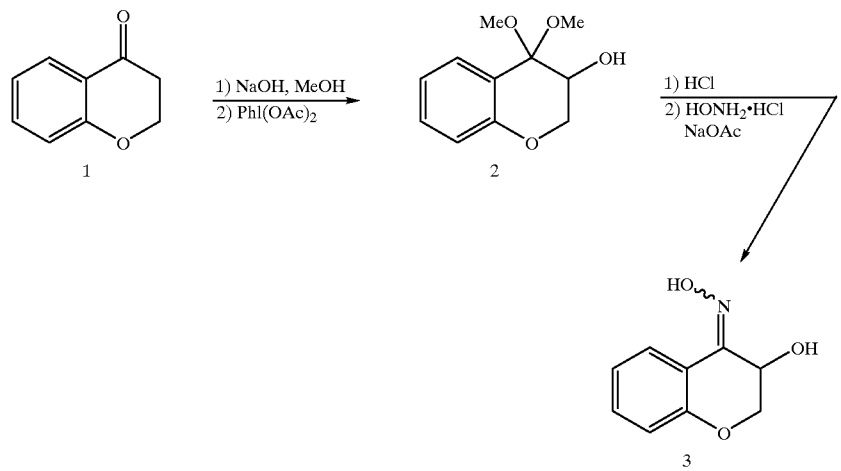

To a solution of NaOH (1.6 Kg, 39 mol, 3.0 equiv. assuming 97% purity) in MeOH (11.1 L) at −10° C. was added a solution of chromanone (1, 2.0 Kg, 13 mol, 1.0 equiv. assuming 99% purity) in MeOH (8.2 L) precooled to −10° C. The resulting yellow solution was aged 5 minutes at −10° C. and a slurry of iodobenzene diacetate (4.44 Kg, 13 mol, 1.00 equiv assuming 97% purity) in MeOH (12.2 L) was added at −10° C. The dark orange reaction mixture was aged 0.5 hour at −10° C. and was warmed to 20° C. over 1 hour. The reaction mixture was aged at 20° C. for 3 hours and was transferred to a solution of 4N aqueous HCl (11.8 L, 45.5 mol, 3.5 equiv.) at 0–20° C. over >10 minutes. The yellow slurry was aged at 20–30° C. for 20 minutes and sodium acetate (2.74 kg, 33.4 mol, 2.5 equiv.) and hydroxylamine hydrochloride (1.86 kg, 26.7 mol, 2.0 equiv) were subsequently added in one portion. The reaction mixture was warmed up to 50° C., aged 1 hour and cooled back to room temperature. The solution was concentrated to a total volume of 28 L, was diluted with water (16 L) and was extracted with heptane (2×16 L). The methanolic aqueous layer was extracted with IPAc (2×16 L). The combined IPAc layers were washed with water (1×16 L), were concentrated and flushed with additional IPAc to a final volume of 5.6 L (KF<400 μg/ml). Heptane (1.9 L) was added over 30 minutes at 20° C., followed by more heptane (18.9 L) added over 30 minutes. The hydroxychromanone oxime 3 crystallized as a yellow solid. The mixture was cooled to −10° C., aged 2 hours, filtered and washed with 3 L of 3.7:1 heptane/IPAc at −10° C. and 3 L of heptane at 20° C. The oxime was dried under vacuum at 20° C. to give a light yellow solid (1.82 Kg, 75%).

$^1$H NMR (400 MHz DMSO-$d_6$) Major isomer: δ9.70–9.93 (br, 1H), 8.35 (dd, 1H, $J_1$=7.8, $J_2$=1.6), 7.86 (dt, 1H, $J_1$=7.8, $J_2$=1.7), 7.54 (dt, 1H, $J_1$=11.7, $J_2$=1.1), 7.49 (dd, 1H, $J_1$=8.2 $J_2$=1.1), 5.68 (t, 1H, $J_1$=2.2), 4.91 (dd, 1H, $J_1$=12.4, $J_2$=2.3), 4.59 (dd, 1H, $J_1$=12.4, $J_2$=2.1), 4.13–4.38 (br, 1H). Selected minor isomer peaks: δ9.13 (dd, 1H, $J_1$=8.1, $J_2$=1.7), 7.91 (dt, 1H, $J_1$=7.9, $J_2$1.7), 4.94 (dd, 1H, $J_1$=9.8, $J_2$=2.6), 4.76 (dd, 1H, $J_1$=12.8, $J_2$=2.8)

Step B: Hydrogenation and Treatment with Base

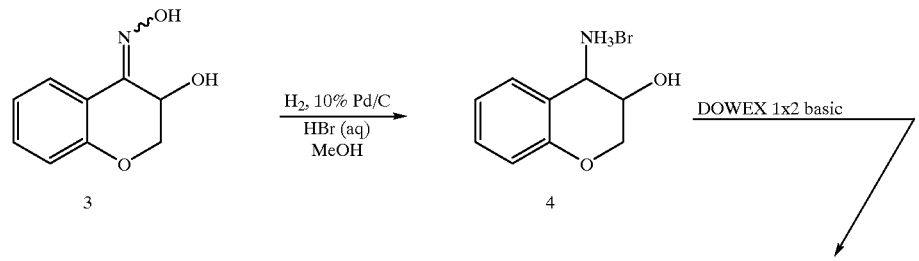

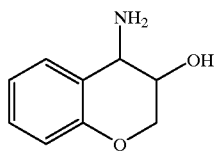

To a solution of oxime (3, 2.51 Kg, 14.02 mol) in methanol (49 L) at 0° C. was charged 48% aqueous HBr (1.94 L) maintaining the temperature below 5° C. 10% Palladium on carbon (2 Kg, 62% water wet) was charged and the mixture was hydrogenated in a five-gallon, stirred autoclave at 5° C., 40 psig for 12 hr (cis/trans 20:1, 89% assay yield of cis isomer). The mixture was filtered through solka floc and washed with methanol to give a solution of the HBr salt 4 in methanol (85 L). The batch was eluted through Dowex 1×2 (19 L) on the base-cycle using methanol (72 L). The solution of free-base amine 5 was solvent switched to ethanol (44 L, KF≦550 ug/mL) under reduced pressure.

Step C: Mandelate Formation

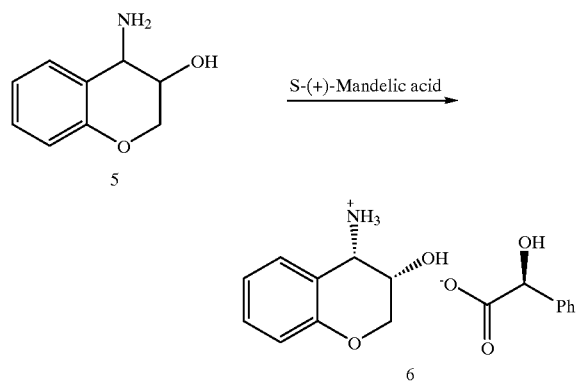

The free base amine in ethanol was heated to 70° C. and S-mandelic acid (2.1 Kg, 14 mol) in ethanol (3 L) was added. The mixture was cooled to 15° C. over 3 hr. The salt 6 was isolated by filtration and washed with ethanol (3.5 L). The batch was dried under vacuum at 20° C. to give 1.688 Kg of dry cake (>96% ee, 38% overall yield).

Step D: Salt Break

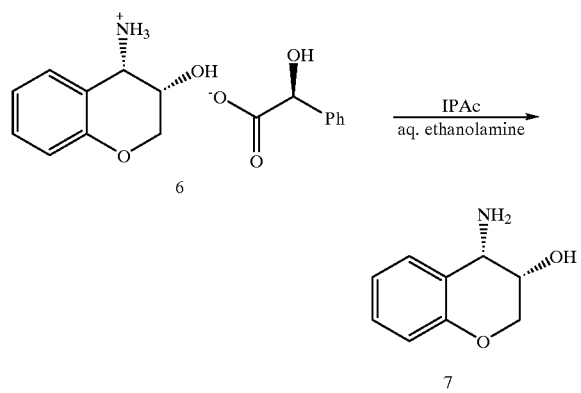

To a slurry of the mandelate salt (6, 1.688 Kg, mol) in isopropylacetate (16 L) at 15–20° C. was added 10% v/v aqueous ethanolamine (6.6 L). The resulting bi-phasic mixture was agitated for 30 minutes and settled for 20 minutes. The phases were cut and the aqueous layer was extracted with IPAc (3×8 L). The IPAc extracts were batch concentrated to 8 L at 40–50° C. (KF≦500 ug/mL). The batch was heated to 65–70° C. and n-heptane (8 L) was added over 30 minutes. The batch was cooled to 0–5° C. over 3 hr and the aminochromanol was isolated by filtration. The wet cake was washed with 1:1 IPAc/n-heptane at 0–5° C. (1.5 L) and dried under vacuum at 20° C. to give S,S-aminochromanol 7 as a colorless solid (0.75 Kg, 90%).

A differential scanning calorimetry curve was obtained for Compound 7 under a nitrogen atmosphere in a closed cup at a heating rate of 10° C./min using a DSC Model 2910 (DuPont Instruments). The curve showed an endotherm, due to melting, with an extrapolated onset temperature of about 110° C., a peak temperature of about 111° C. and an associated heat of about 193 Joules/gram. An X-ray powder diffraction pattern was also obtained for Compound 7 using a Philips Diffractometer APD 3720 with copper K alpha radiation. The following d-spacings were observed: 7.77, 7.54, 4.74, 4.62, 4.49, 4.47, 4.39, 3.98, 3.90, 3.78, 3.64, 3.30, 3.04, 2.70, 2.66, 2.61, 2.58, 2.53, and 2.43 angstroms. The specific rotation (1% solution in MeOH, 405 nm) was +177.9.

EXAMPLE 2

Preparation of R,R-Aminochromanol

R,R-Aminochromanol 8 was prepared using a procedure analogous to that described in Example 1 for the preparation of S,S-aminochromanol 7, except that in Step C R-mandelic acid was used instead of S-mandelic acid. A DSC curve obtained for 8 in the same manner as described for 7 in Example 1, Step D, showed an endotherm, due to melting, with an extrapolated onset temperature of about 110° C., a peak temperature of about 112° C. and an associated heat of about 190 Joules/gram. The following d-spacings were observed for 8 in an XRPD pattern obtained as in Example 1, Step D: 7.84, 7.60, 4.77, 4.64, 4.49, 4.41, 4.00, 3.94, 3.92, 3.79, 3.69, 3.65, 3.32, 2.91, 2.67, 2.58, and 2.53 angstroms. The specific rotation (1% solution in MeOH, 405 nm) was −179.8.

EXAMPLE 3

Hydrogenation of Compound 3

A series of hydrogenations of compound 3 in methanol was conducted with various acids and catalysts in accordance with the procedure described in Step B of Example 1, and the relative amounts of cis and trans isomers in product 5 were determined. The experimental conditions employed in these hydrogenations and the results thereof are shown in the following Table:

| Acid | Catalyst | cis/trans Selectivity |
|---|---|---|
| — | Pd/C | 1.5:1 |
| HBr | Pd/C | 12.5:1 |
| HBr | Pd black | 13.9:1 |
| HCl | Pd black | 1.5:1 |
| HNO$_3$ | Pd/C | 2.1:1 |
| H$_2$SO$_4$ | Pd/C | 1.9:1 |
| acetic acid | Pd/C | 1.5:1 |
| methanesulfonic acid | Pd/C | 4.7:1 |

The hydrogenation was conducted at 15–25° C. and with 40 psig H$_{2.1}$ equivalent of acid was employed per equivalent of hydroxy oxime. The acids were charged to the reactor as 48% aqueous HBr, conc. HCl, conc. HNO$_3$, conc. H$_2$SO$_4$, glacial acetic acid, and pure methanesulfonic acid respectively.

EXAMPLE 4

Hydrogenation of the O-Benzyl Oxime 7

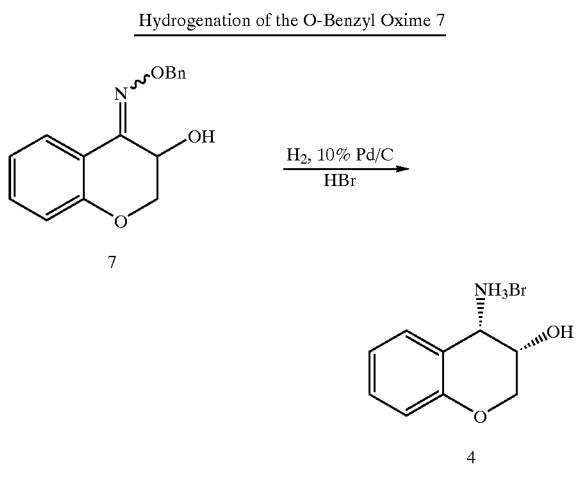

The O-benzyloxime 7 was hydrogenated in accordance with the procedure described in Step B of Example 1 in the absence of an acid and in the presence of HBr (1 equivalent per equivalent of oxime). The cis/trans ratios of the resulting products were 1.8:1 (no acid) and 8:1 (HBr).

EXAMPLE 5

Hydrogenation of Compound 3

A second series of hydrogenations of compound 3 in methanol was conducted with various acids in accordance with the procedure described in Step B of Example 1, wherein the hydrogenations were run with 1 equivalent of acid at 40 psig for 12 hours at 10° C,. 0.3M in methanol and with 3 mol % Pd/C catalyst. The relative amounts of cis and trans isomers in product 5 were determined. Assay yields were also determined via HPLC. The results are shown in the following Table:

| Acid | cis/trans Selectivity | Assay Yield (%) |
|---|---|---|
| — | 1.3:1 | 96 |
| HF | 2.2:1 | 79 |
| HCl | 7:1 | 95 |
| HBr | 23:1 | 94 |
| HI | — | 0 |
| CF$_3$SO$_3$H | 3.2:1 | 90 |
| acetic acid | 1.5:1 | 87 |
| CF$_3$CO$_2$H | 1.7:1 | 92 |
| B(OH)$_3$ | 1.4:1 | 90 |

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a cis-aminochromanol of Formula (I):

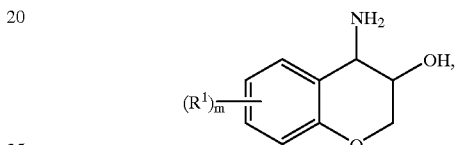

which comprises:
(A) hydrogenating in the presence of a catalyst a mixture comprising an oxime of Formula (II):

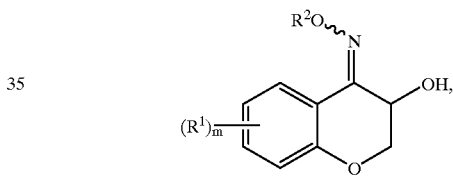

solvent, and an acid selected from the group consisting of (i) HBr, (ii) HCl, and (iii) organic sulfonic acids; wherein each $R^1$ is independently halo, $C_1$–$C_6$ alkyl, halogenated $C_1$–$C_6$ alkyl, $C_1$–$C_6$ alkoxy, halogenated $C_1$–$C_6$ alkoxy, —CO$_2$R$^a$, —COR$^a$, —NR$^a$R$^b$, —NR$^a$—COR$^b$, —NR$^b$—CO$_2$R$^b$, —CO—NR$^a$R$^b$, —OCO—NR$^a$R$^b$, —NR$^a$CO—NR$^a$R$^b$, —S(O)$_p$—R$^a$, wherein p is an integer from 0 to 2, —S(O)$_2$—NR$^a$R$^b$, —NR$^a$S(O)$_2$—R$^b$, or —NR$^a$S(O)$_2$—NR$^a$R$^b$;

$R^2$ is
(1) hydrogen;
(2) $C_1$–$C_6$ alkyl;
(3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl, or phenyl;
(4) $C_3$–$C_8$ cycloalkyl;
(5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl;
(6) phenyl; or
(7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo;

each $R^a$ and $R^b$ is independently hydrogen, $C_1$–$C_4$ alkyl, or $(CH_2)_{0-3}CF_3$; and m is an integer from 0 to 4.

2. The process according to claim 1, wherein the organic sulfonic acid is of formula $R^*$—$SO_2H$; wherein $R^*$ is $C_1$–$C_6$ alkyl, fluorinated $C_1$–$C_6$ alkyl, phenyl, or substituted phenyl wherein each of the substituents on substituted phenyl is independently $C_1$–$C_{12}$ alkyl, $C_1$–$C_{12}$ haloalkyl, halo, cyano, nitro, $C_1$–$C_6$ alkoxy, $C_2$–$C_8$ alkoxyalkyl, $N(R^c R^d)_2$, and $NR^c COR^d$; wherein each $R^c$ and $R^d$ is independently hydrogen, $C_1$–$C_6$ alkyl, or $(CH_2)_{0-4}CF_3$.

3. The process according to claim 1, wherein the hydrogenation catalyst comprises palladium, rhenium, rhodium, platinum, or nickel.

4. The process according to claim 3, wherein the hydrogenation catalyst comprises palladium.

5. The process according to claim 1, wherein the acid is HBr, HCl, or methanesulfonic acid.

6. The process according to claim 5, wherein the acid is HBr.

7. The process according to claim 6, wherein the catalyst is Pd/C.

8. The process according to claim 1, wherein the solvent in step A is selected from the group consisting of $C_3$–$C_{12}$ linear and branched alkanes, $C_2$–$C_6$ linear and branched halogenated alkanes, $C_5$–$C_7$ cycloalkanes, $C_6$–$C_{10}$ aromatic hydrocarbons, dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, and $C_1$–$C_6$ alkyl alcohols.

9. The process according to claim 1, wherein the hydrogenation is conducted at a temperature in the range of from about –20 to about 100° C. and at a pressure of at least about 2 psig (115 kPa).

10. The process according to claim 1, wherein $R^2$ is hydrogen, $C_1$–$C_4$ alkyl, phenyl, or benzyl.

11. The process according to claim 10, wherein $R^2$ is hydrogen.

12. The process according to claim 1, which further comprises:
(B) treating the hydrogenated mixture with base to provide free amine.

13. The process according to claim 12, wherein in step B the treatment with base comprises eluting the hydrogenated mixture through an ion exchange column.

14. The process according to claim 12, which further comprises:
(C) resolving the S,S- and R,R-isomers of Compound I by
(c1) forming a solution of Compound I with a chiral acid, and
(c2) crystallizing from the solution a salt which contains predominantly either the S,S- or R,R-isomer.

15. The process according to claim 14, wherein step C further comprises:
(c3) recovering a salt which contains predominantly the other of the S,S- and R,R-isomers from the mother liquor.

16. The process according to claim 14, wherein step C further comprises:
(c4) breaking the crystallized salt of the recovered isomer by treating the salt with base.

17. The process according to claim 14, wherein the chiral acid is (S)-mandelic acid or (R)-mandelic acid.

18. The process according to claim 17, wherein the chiral acid is (S)-mandelic acid, and the crystallized (S)-mandelate salt is a salt of the S,S-isomer.

19. The process according to claim 18, which further comprises:
(c4') breaking the recovered (S)-mandelate salt with ethanolamine to provide an S,S-aminochromanol of Formula (I')

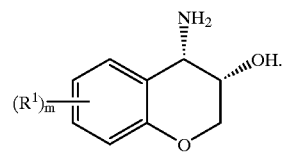

20. The process according to claim 1, which is a process for preparing cis-aminochromanol 5:

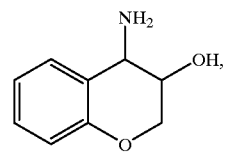

which comprises
(A) hydrogenating a mixture comprising oxime 3:

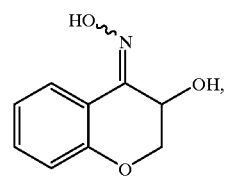

and solvent in the presence of a catalyst and in the presence of an acid selected from the group consisting of (i) HBr, (ii) HCl, and (iii) organic sulfonic acids; and
(B) treating the hydrogenated mixture with base.

21. The process according to claim 20, wherein the catalyst is a palladium catalyst.

22. The process according to claim 20, wherein the acid is HBr.

23. The process according to claim 22, wherein the catalyst is Pd/C.

24. The process according to claim 20, wherein the hydrogenation is conducted at a temperature in the range of from about –20 to about 100° C. and at a pressure of at least about 2 psig (115 kPa).

25. The process according to claim 20, wherein
the catalyst is a palladium catalyst;
the acid is aqueous HBr; and
the hydrogenation is conducted at a temperature in the range of from about –20 to about 100° C. and at a pressure of at least about 2 psig (115 kPa).

26. The process according to claim 20, wherein
the catalyst is a palladium catalyst;
the acid is aqueous KBr;
the amount of acid is in the range of from about 0.95 to about 1.05 equivalents per equivalent of 3; and
the hydrogenation is conducted at a temperature in the range of from about –5 to about 5° C.

27. The process according to claim 20, which further comprises:

(C) resolving the S,S-isomer of 5 by
  (c1) forming a solution of 5 with (S)-mandelic acid, and
  (c2) crystallizing from the solution a salt of the S,S-isomer.

28. The process according to claim 27, wherein step C further comprises:
  (c4) breaking the (S)-mandelate salt with ethanolamine to provide S,S-aminochromanol 7:

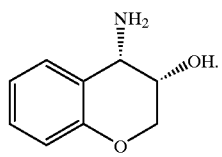

29. A process for improving the optical purity of S,S-aminochromanol 7:

with which at least some R,R-isomer is present, wherein the process comprises:
  (a) forming a solution of the cis-aminochroman-3-ol with (S)-mandelic acid;
  (b) crystallizing the (S)-mandelate salt from the solution; and
  (c) breaking the (S)-mandelate salt with base to provide 7 having greater optical purity.

30. The process according to claim 28, wherein the base in step (c) comprises ethanolamine.

* * * * *